US00PP35521P2

(12) United States Plant Patent
Freer

(10) Patent No.: US PP35,521 P2
(45) Date of Patent: Dec. 5, 2023

(54) ***GEUM* PLANT NAMED 'STOCRGEU'**

(50) Latin Name: ***Geum* hybrid**
Varietal Denomination: STOCRGEU

(71) Applicant: Gregory Freer, Cheshire (GB)

(72) Inventor: Gregory Freer, Cheshire (GB)

( * ) Notice: Subject to any disclaimer, the term of this patent is extended or adjusted under 35 U.S.C. 154(b) by 0 days.

(21) Appl. No.: 18/105,351

(22) Filed: Feb. 3, 2023

(30) Foreign Application Priority Data

Apr. 22, 2022 (QZ) ..... PBR 2022/1073

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
CPC ..... A01H 5/02; A01H 5/00; A01H 6/74
See application file for complete search history.

(56) References Cited

U.S. PATENT DOCUMENTS

PP28,476 P2 * 10/2017 MacGregor ..... A01H 6/74
Plt./263.1

* cited by examiner

*Primary Examiner* — June Hwu
(74) *Attorney, Agent, or Firm* — Penny J. Aguirre

(57) ABSTRACT

A new cultivar of hybrid *Geum* plant named 'STOCRGEU' that is characterized by its strong growing habit, its compact plant habit, its flowers that are large in size and facing upward, and its flowers that are bright red in color.

2 Drawing Sheets

Botanical classification: *Geum* hybrid.
Variety denomination: 'STOCRGEU'.

CROSS-REFERENCE TO A RELATED APPLICATION

This application claims priority to European Community Plant Variety Office (CPVO) Plant Breeder's Rights Application No. 2022/1073 filed on Apr. 22, 2022, under 35 U.S.C. 119(f), the entire contents of which is incorporated by reference herein. The Applicant received the information for the Plant breeders' rights application directly from the Inventor.

BACKGROUND OF THE INVENTION

The present invention relates to a new and distinct cultivar of *Geum* plant, botanically of hybrid origin and known as *Geum* 'STOCRGEU' and will be referred to hereinafter by its cultivar name, 'STOCRGEU'. The new cultivar of *Geum* is an herbaceous perennial grown for landscape and container use.

The new cultivar arose from an ongoing breeding program conducted by the Inventor in Knutsford, Cheshire, The United Kingdom. The new cultivar arose from open pollination of both unnamed and unpatented seedlings from the Inventor's breeding program and cultivars of *Geum rivale* and *Geum coccineum* in June of 2017. The seeds were pooled after collection and therefore the exact parents are unknown, however the new cultivar is believed to be a hybrid of *Geum rivale* and *Geum coccineum* based on its characteristics. 'STOCRGEU' was selected as a single unique plant from the seedling that resulted from sowing the mixture of seeds in August of 2018.

Asexual propagation of the new cultivar was first accomplished by division in Cheshire, United Kingdom in August 2018 under the direction of the Inventor. Asexual propagation by division has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'STOCRGEU' as a unique cultivar of *Geum*.

1. 'STOCRGEU' exhibits a strong growing habit.
2. 'STOCRGEU' exhibits a compact plant habit.
3. 'STOCRGEU' exhibits flowers that are large in size and facing upward.
4. 'STOCRGEU' exhibits flowers that are bright red in color.

'STOCRGEU' can be most closely compared to *Geum* cultivars 'Macgeu001' (U.S. Plant Pat. No. 28,476) and 'Tropical Tempest' (not patented). 'Macgeu001' differs from 'STOCRGEU' in having flowers that are lighter red in color with apricot shadings, a taller plant height, and a more open and lax plant habit. 'Tropical Tempest' differs from 'STOCRGEU' in having a taller plant height and flowers that are red-orange in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Visions Pictures, Plantipp, Posadzone, and Rijnbeek Perennials (facebook).

BRIEF DESCRIPTION OF THE DRAWINGS

The accompanying color photographs illustrate the overall appearance and distinct characteristics of the new *Geum*. The photographs were taken of a 2-year-old plant of 'STOCRGEU' as grown outdoors in a 17-cm container in Boskoop, The Netherlands.

The photograph in FIG. 1 provides a view of the plant habit of 'STOCRGEU' in bloom.

Figure 1:
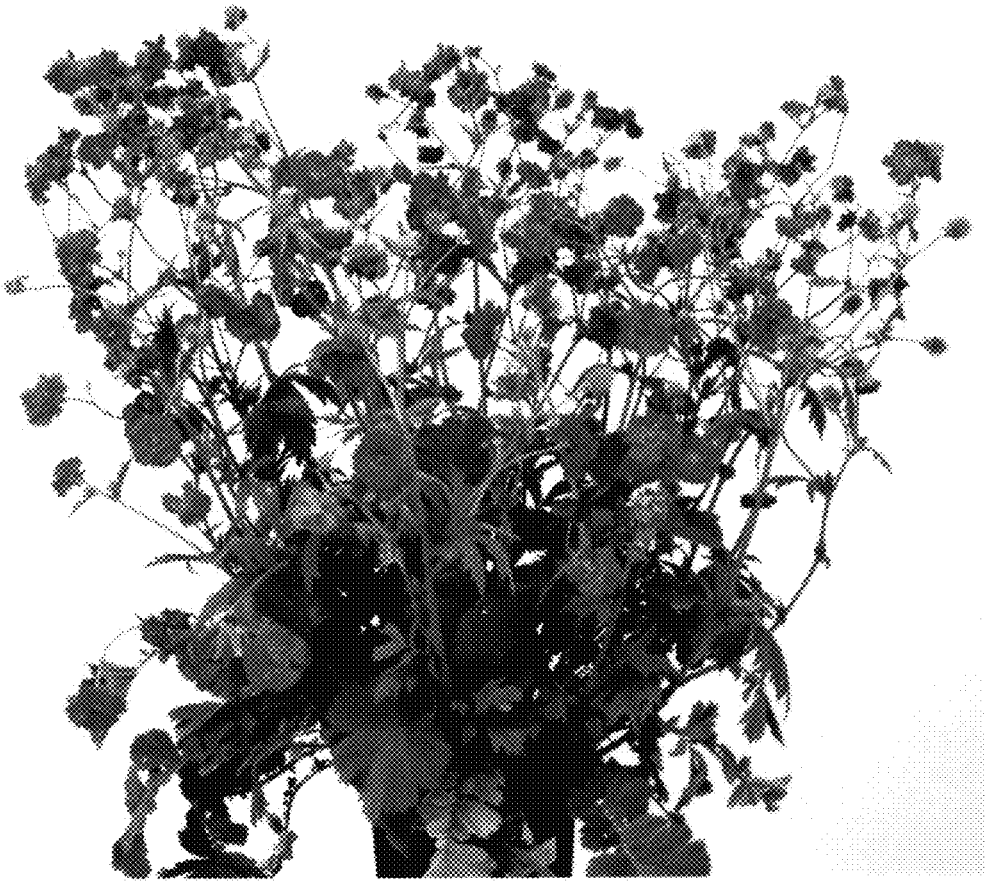
Figure 2:
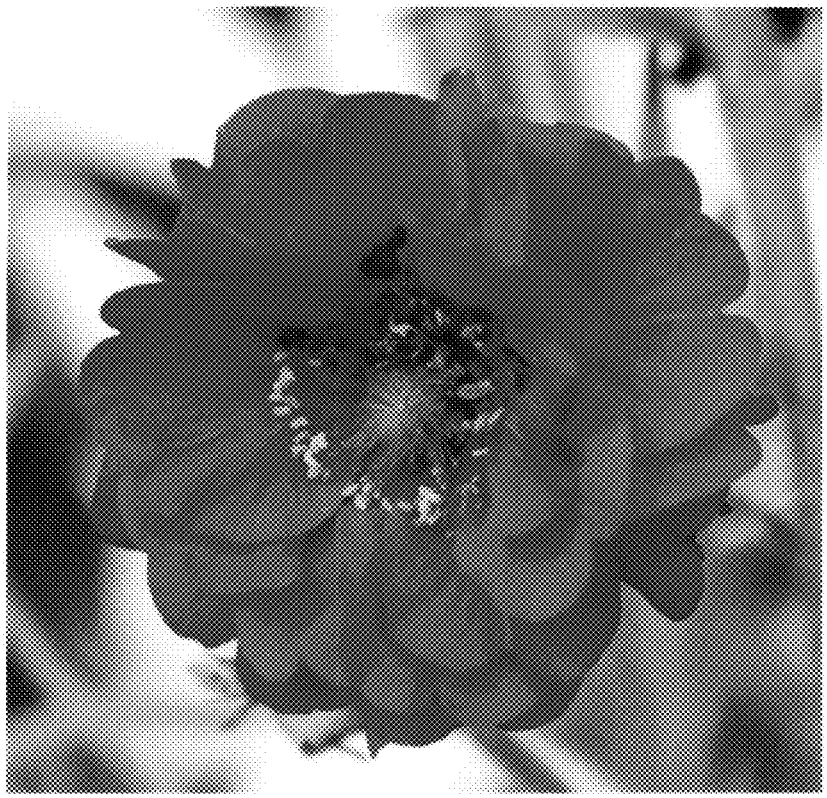

The photograph in FIG. 2 provides a close-up view of a flower of 'STOCRGEU'.

Figure 3:
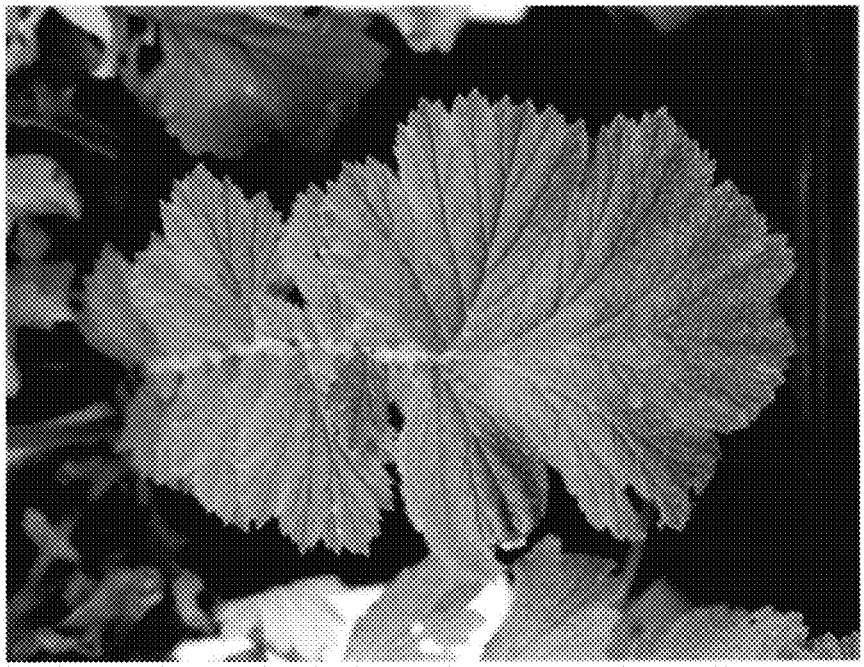

The photograph in FIG. 3 provides a close-up view of the foliage of 'STOCRGEU'.

The colors in the photographs are as close as possible with the photographic and printing technology utilized and the color values cited in the detailed botanical description accurately describe the colors of the new *Geum*.

DETAILED BOTANICAL DESCRIPTION

The following is a detailed description of 2-year-old plants of 'STOCRGEU' as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—12 weeks from spring into summer in the United Kingdom.

*Plant type*.—Herbaceous perennial.

*Plant habit*.—Strong and compact.

*Height and spread*.—Average of 45 cm in height (foliar plane), 57.5 cm in height (floral plane), 89 cm in diameter as a 2-year-old plant in a 17-cm container.

*Hardiness*.—At least in U.S.D.A Zones 5 to 9.

*Diseases and pests*.—No susceptibility or resistance to pests has been observed.

*Root description*.—Fibrous and fine.

*Propagation*.—Division.

*Root development*.—Crop time to a finished flowering plant is approximately 35 weeks from propagation.

*Growth rate*.—Highly vigorous.

Branch description:

*Branch shape*.—Rounded.

*Branch color*.—Young; 144B, mature; 146B.

*Branch size*.—Average of 39.3 cm in length, 5 mm in diameter.

*Branch strength*.—Strong.

*Branch surface*.—Slightly glossy, densely pubescent, average of 0.2 cm in length, 155A in color.

*Branch aspect*.—Average of 40° to vertical (varying between 0° and 80°).

*Branching quantity*.—An average of 35 main branches.

*Internode length*.—An average of 7.6 cm.

Foliage description:

*Leaf division*.—Simple.

*Leaf margins*.—Basal leaves; serrate to biserrate, stem leaves coarsely serrate to incised, both lobed; deeply lobed to nearly cleft, sinus depth; deep, sinus orientation; divergent.

*Leaf size*.—Basal leaves; 32.1 cm in length, 10.8 cm in width, stem leaves; 8.7 cm in length, 6.2 cm in width.

*Leaf shape*.—Basal leaves; lyrate, stem leaves; lyrate to trifoliate and deeply lobed near cleft.

*Leaf base*.—Broadly acuminate.

*Leaf apex*.—Basal leaves; praemorse, stem leaves; narrowly acute.

*Leaf venation*.—Pinnate, basal and stem leaves color upper surface; 146B, basal leaves lower surface; N144A, stem leaves lower surface 144C.

*Leaf attachment*.—Petiolate.

*Leaf arrangement*.—Alternate.

*Leaf surface*.—Both surfaces of leaves are matte, smooth, and densely covered with soft strigose hairs, 155C in color, an average of 1.25 mm in length on upper side, 0.75 mm in length on the lower side.

*Leaf color*.—Young upper surface 143B, young lower surface 144B, mature upper surface NN137B, mature lower surface 147B.

*Petioles/rachis*.—Basal leaves (rachis); average of 24.2 cm in length, 4 mm in diameter, moderately strong, surfaces matte and densely covered with soft hairs, an average of 2 mm in length, 156D in color, color; upper surface 146A, lower surface 144A, stem leaves (petiole/rachis); average of 1.6 cm in length, 2 mm in diameter, moderately strong, surfaces are matte and densely covered with soft hairs, an average of 2 mm in length, 156D in color, color; upper surface 146B, lower surface 144B.

*Stipules*.—At the base of each stem are 2 leafy stipules; broadly ovate to cleft in shape (3-lobed), serrate margins, 2.6 cm in length, 2.3 cm in width, apex is narrowly acute, base is cuneate, surfaces are matte and densely covered with soft hairs, an average of 2 mm in length, 156D in color.

Flower description:

*Inflorescence type*.—Compound cyme.

*Inflorescence size*.—Average of 25.9 cm in height, 19.1 cm in width.

*Inflorescence lastingness*.—Average of 10 days, self-cleaning.

*Flower shape*.—Semi-double.

*Flower fragrance*.—None.

*Flower quantity*.—Average of 11 flowers per inflorescence, 250 flowers per plant.

*Flower arrangement*.—Rotate.

*Flower aspect*.—Upright to outward.

*Flower size*.—Average of 4.6 cm in height and diameter, 2.5 cm in depth.

*Flower buds*.—Average of 1 cm in length, 9 mm in diameter, broadly ovate in shape, surface is smooth, matte and densely covered with soft hairs, an average of 1.25 mm in length, N155A in color, bud color; 144B, immature petals 22A.

*Peduncles*.—Moderately strong to strong in strength, average of 18.8 cm in length, 3 mm in diameter, held in a vertical angle, surface is smooth, matte, and densely covered with soft pubescence, average of 2 mm in length, 155A in color, color; 146B to 146C.

*Pedicels*.—Moderately strong in strength, average of 4.2 cm in length, 1.75 mm in diameter, held in a 35° angle, surface is smooth, matte, and densely covered with soft pubescence, average of 1.5 mm in length, 155A in color, color; 144A.

*Calyx*.—Rotate-shaped, average of 1 cm in length and 1.3 cm in diameter.

*Sepals*.—10 (5 large, 5 small), 1 whorled row, large sepals; average of 1 cm in length, 6 mm in width, deltoid in shape, acute apex, straight base, entire margins, both surfaces are smooth and matte, upper surface is moderately covered with soft hairs, 0.5 mm in length, too small to measure color, lower surface and margins are moderately to densely covered with soft hairs an average of 0.5 mm, too small to measure color, color: when opening and fully open upper and lower surface 144A.

*Petals*.—Rotate, average of 30, 5 whorls, base is unfused and broadly attenuate in shape, average of 1.8 cm in length, 1.9 cm in width, reniform to broadly obovate in shape, apex is emarginate to broadly emarginate in shape, margins are entire with medium to high undulation, both surfaces are matte and non-rugose, upper surface is glabrous, smooth, slightly velvety, lower surface is glabrous, smooth, non-velvety, color: when opening upper surface; 34A, when opening lower surface; 34B, when fully open upper surface; N34B, petal venation N34B, fading to 34A, when fully open lower surface; 34A, petal venation N34C, fading to N34C.

*Floral bracts*.—None.

Reproductive organs:

*Gynoecium*.—Pistil; 60, 5 mm in length, stigma; pointed, 0.5 mm in length and diameter, 34B in color, style; 4.5 mm in length and 33B in color, ovary; 145A in color.

*Androecium*.—Stamens: 120, anthers; dorsifixed, oblong in shape, 1.5 mm in length, 0.5 mm in width, 15A to 15B in color, filaments; 4 mm in length, color; 22A, base 13A, pollen; low in quantity, 15A to 15B in color.

*Fruit and seed*.—Seed; average of 1 per fruit, 2 mm in length, 1 mm in diameter, surface is smooth and glabrous, 199B in color, fruit; average of 23,000 fruit per plant, 1.1 cm in length, 2.5 mm in diameter, surface is densely pubescent with short soft hairs, 2 mm in length, NN155B in color, color: 145B, top 144A, persistent style 173A.

It is claimed:

1. A new and distinct cultivar of *Geum* plant named 'STOCRGEU' as herein illustrated and described.

* * * * *